(12) United States Patent
Fukushima et al.

(10) Patent No.: US 7,935,846 B2
(45) Date of Patent: May 3, 2011

(54) METHOD OF PRODUCING NITROGEN-CONTAINING COMPOUND

(75) Inventors: Tetsuaki Fukushima, Wakayama (JP); Hideki Taniguchi, Wakayama (JP); Michio Terasaka, Wakayama (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 12/520,739

(22) PCT Filed: Oct. 17, 2007

(86) PCT No.: PCT/JP2007/070257
§ 371 (c)(1),
(2), (4) Date: Jun. 22, 2009

(87) PCT Pub. No.: WO2008/081635
PCT Pub. Date: Jul. 10, 2008

(65) Prior Publication Data
US 2009/0292145 A1    Nov. 26, 2009

(30) Foreign Application Priority Data

Dec. 28, 2006  (JP) ................................ 2006-355014
Jul. 13, 2007  (JP) ................................ 2007-183990

(51) Int. Cl.
*C07C 209/78* (2006.01)
*C07C 291/04* (2006.01)

(52) U.S. Cl. ...................................... 564/488; 564/298

(58) Field of Classification Search ........................ None
See application file for complete search history.

(56) References Cited

U.S. PATENT DOCUMENTS

| | | | |
|---|---|---|---|
| 4,937,384 A | | 6/1990 | Dobson |
| 5,075,505 A | * | 12/1991 | Forquy et al. ................. 564/488 |
| 2006/0287556 A1 | | 12/2006 | Loenders et al. |

FOREIGN PATENT DOCUMENTS

| | | |
|---|---|---|
| DE | 1493839 A | 3/1970 |
| JP | 9-241222 | 9/1997 |
| JP | 2001 302596 | 10/2001 |
| JP | 2007 269788 | 10/2007 |

OTHER PUBLICATIONS

U.S. Appl. No. 12/676,188, filed Mar. 3, 2010, Terasaka et al.
U.S. Appl. No. 12/672,327, filed Feb. 5, 2010, Terasaka et al.

* cited by examiner

*Primary Examiner* — Brian J Davis
(74) *Attorney, Agent, or Firm* — Oblon, Spivak, McClelland, Maier & Neustadt, L.L.P.

(57) ABSTRACT

The present invention provides a process for producing high-purity aliphatic tertiary amines containing a less amount of by-products by using a chromium-free catalyst with a good productivity in an economically advantageous manner. The present invention relates to a process for producing a tertiary amine by reducing an amide compound in the presence of a catalyst containing copper and magnesium at a molar ratio of magnesium to copper (magnesium/copper) of from 0.01 to 20.

20 Claims, No Drawings

METHOD OF PRODUCING NITROGEN-CONTAINING COMPOUND

TECHNICAL FIELD

The present invention relates to a process for producing nitrogen-containing compounds, and more particularly, to a process for producing tertiary amines.

BACKGROUND ART

Aliphatic tertiary amines are important intermediate products of fabric softeners, antistatic agents, additives for gasoline, shampoos, rinses, bactericides, detergents, etc., and have been used in extensive domestic and industrial application fields.

As the method for producing the aliphatic tertiary amines, there is known an amide reduction method in which an amide compound obtained from inexpensive regenerative fatty acids is used as a raw material. As the amide reduction method, there are conventionally known various methods using a copper/chromium-based catalyst, a noble metal-based catalyst, etc. For example, Patent document 1 discloses the method using a noble metal-based catalyst. However, the method described in Patent document 1 inevitably requires to use a solvent, resulting in problems such as poor productivity. In Patent Document 2, it has been attempted to enhance a dehydration efficiency and improve a reactivity by physically adding zeolite to a palladium/rhenium catalyst. However, the method described in Patent document 2 requires a high reaction pressure. Also, Patent Document 3 discloses the method using a copper/chromium-based catalyst. However, the method described in Patent document 3 also requires a high reaction pressure as well as a large burden of facilities. Patent Document 4 discloses the method of enhancing a durability of a copper/chromium-based catalyst by adding manganese thereto. However, the method described in Patent Document 4 also requires a high reaction pressure and flowing a large excess amount of hydrogen through the reaction system. Further, Patent Document 5 discloses the method of reducing an amide using a hydrogenation catalyst, in which a copper/chromium-based catalyst is mentioned as a preferred example of the hydrogenation catalyst. However, these catalysts used in the above conventional methods must be handled with great care to ensure a safety, etc., upon disposal. Therefore, there is a demand for development of chromium-free catalysts.

Patent Document 6 discloses the method using a chromium-free copper-based catalyst such as a copper/zinc catalyst, a copper/zinc/ruthenium catalyst and a copper/nickel/ruthenium catalyst. However, this method is still unsatisfactory in reaction selectivity.

Patent Document 1: JP 9-241222A
Patent Document 2: JP 63-255253A
Patent Document 3: DP 1493839A
Patent Document 4: U.S. Pat. No. 5,075,505
Patent Document 5: USP 2006-287556A
Patent Document 6: JP 2001-302596A

DISCLOSURE OF THE INVENTION

Problem to be Solved by the Invention

The present invention is directed to a process for producing high-purity aliphatic tertiary amines containing a less amount of by-products by using a chromium-free catalyst with a good productivity in an economically advantageous manner.

Means for Solving Problem

Thus, the present invention relates to a process for producing a tertiary amine represented by the following general formula (II):

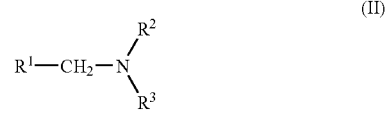

(II)

wherein $R^1$ is a linear or branched aliphatic hydrocarbon group having 5 to 23 carbon atoms; and $R^2$ and $R^3$ are each independently a linear or branched alkyl group having 1 to 6 carbon atoms and may be the same or different, said process including the step of reducing an amide compound represented by the following general formula (I):

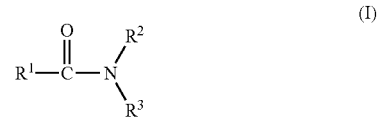

(I)

wherein $R^1$, $R^2$ and $R^3$ are the same as defined above, in the presence of a catalyst containing copper and magnesium at a mass ratio of magnesium to copper (magnesium/copper) of from 0.01 to 20.

Effect of the Invention

In accordance with the process of the present invention, a high-purity aliphatic tertiary amine containing a less amount of by-products can be produced with a high productivity in an economically advantageous manner by reducing an amide compound under moderate conditions. In addition, since a chromium-free catalyst is used in the process, the used catalyst can be subjected to disposal treatment with a high safety.

BEST MODE FOR CARRYING OUT THE INVENTION

In the process of the present invention, a tertiary amine represented by the following general formula (II):

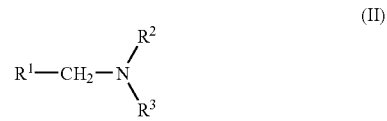

(II)

wherein $R^1$ is a linear or branched aliphatic hydrocarbon group having 5 to 23 carbon atoms; and $R^2$ and $R^3$ are each independently a linear or branched alkyl group having 1 to 6 carbon atoms and may be the same or different, is produced by reducing an amide compound represented by the following general formula (I):

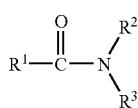

(I)

wherein $R^1$, $R^2$ and $R^3$ are the same as defined above,
in the presence of a catalyst.

In each of the above general formulae (I) and (II), $R^1$ represents a linear or branched aliphatic hydrocarbon group having 5 to 23 carbon atoms. The aliphatic hydrocarbon group may be either saturated or unsaturated. Meanwhile, the branched aliphatic hydrocarbon group involves an alicyclic group.

Examples of $R^1$ in each of the above general formulae (I) and (II) include various hexyl groups, various heptyl groups, various octyl groups, various nonyl groups, various decyl groups, various undecyl groups, various dodecyl groups, various tridecyl groups, various tetradecyl groups, various pentadecyl groups, various hexadecyl groups, various heptadecyl groups, various octadecyl groups, various nonadecyl groups, various eicosanyl groups, various heneicosanyl groups, various docosanyl groups, various tricosanyl groups, various tetracosanyl groups, various heptenyl groups, various octenyl groups, various nonenyl groups, various decenyl groups, various undecenyl groups, various dodecenyl groups, various tridecenyl groups, various tetradecenyl groups, various pentadecenyl groups, various hexadecenyl groups, various heptadecenyl groups, various octadecenyl groups, various nonadecenyl groups, various icosenyl groups and various docosenyl groups.

Among these groups as $R^1$, from the viewpoint of usefulness of the obtained tertiary amines, preferred are linear or branched alkyl or alkenyl groups having 5 to 21 carbon atoms, and more preferred are various pentyl groups, various heptyl groups, various nonyl groups, various undecyl groups, various tridecyl groups, various pentadecyl groups, various heptadecyl groups, various nonadecyl groups, various heneicosanyl groups, various heptenyl groups, various nonenyl groups, various undecenyl groups, various tridecenyl groups, various pentadecenyl groups, various heptadecenyl groups, various nonadecenyl groups and various heneicosenyl groups. The term "various" as used herein means all of those groups having a linear chain or a branched chain.

In each of the above general formulae (I) and (II), $R^2$ and $R^3$ are each independently a linear or branched alkyl group having 1 to 6 carbon atoms. Meanwhile, the "branched alkyl group" also includes a cycloalkyl group. Examples of each of $R^2$ and $R^3$ include methyl, ethyl, n-propyl, isopropyl, n-butyl, isobutyl, sec-butyl, tert-butyl, various pentyl groups, various hexyl groups, cyclopentyl and cyclohexyl. Among these alkyl groups, from the viewpoint of usefulness of the obtained tertiary amines, preferred are linear alkyl groups having 1 to 4 carbon atoms, and more preferred are methyl, ethyl and propyl.

Meanwhile, $R^2$ and $R^3$ may be the same or different from each other.

Examples of the amide compound represented by the above general formula (I) include N,N-dimethyl aliphatic acid amides such as N,N-dimethyl caprylamide, N,N-dimethyl 2-ethylhexane amide, N,N-dimethyl caprinamide, N,N-dimethyl lauroyl amide, N,N-dimethyl myristoyl amide, N,N-dimethyl palmitoyl amide, N,N-dimethyl stearoyl amide, N,N-dimethyl isostearoyl amide, N,N-dimethyl oleyl amide and N,N-dimethyl behenyl amide; and compounds obtained by replacing the N,N-dimethyl group of these aliphatic acid amides with N,N-diethyl, N,N-dipropyl, N-ethyl-N-methyl, N-methyl-N-propyl or N-ethyl-N-propyl. Among these amide compounds, from the viewpoint of usefulness of the obtained tertiary amines, preferred are N,N-dimethyl, N,N-diethyl or N-ethyl-N-methyl aliphatic amides having 8 to 22 carbon atoms.

On the other hand, examples of the tertiary amine represented by the above general formula (II) include amine compounds corresponding to the above exemplified amide compounds of the general formula (I). Specific examples of the tertiary amine include N,N-dimethyl aliphatic amines such as N,N-dimethyl octyl amine, N,N-dimethyl 2-ethylhexyl amine, N,N-dimethyl decyl amine, N,N-dimethyl lauryl amine, N,N-dimethyl myristyl amine, N,N-dimethyl hexadecyl amine, N,N-dimethyl stearyl amine, N,N-dimethyl isostearyl amine, N,N-dimethyl oleyl amine and N,N-dimethyl behenyl amine; and compounds obtained by replacing the N,N-dimethyl group of these aliphatic amines with N,N-diethyl, N,N-dipropyl, N-methyl-N-propyl, N-ethyl-N-methyl, N-methyl-N-propyl or N-ethyl-N-propyl. Among these amine compounds, preferred are those tertiary amines corresponding to the preferred amide compounds exemplified above.

The catalyst used in the present invention is a catalyst containing copper and magnesium at a mass ratio of magnesium to copper (magnesium/copper) of from 0.01 to 20. From the viewpoints of a high catalytic activity and a high selectivity of the catalyst, examples of the preferred catalyst include a supported copper catalyst or a supported copper/magnesium catalyst which is formed by supporting copper, or copper and magnesium, on a carrier composed of a magnesium-containing metal oxide such as magnesia, magnesium-containing hydrotalcite, silica-magnesia and magnesia-alumina, and a supported copper/magnesium catalyst which is formed by supporting copper and magnesium on a carrier composed of silica, alumina, zeolite, diatomaceous earth, titania, zirconia, activated carbon, etc. Among these catalyst, more preferred are the supported copper/magnesium catalyst which is formed by supporting copper and magnesium on a carrier composed of silica, alumina, zeolite or diatomaceous earth, and the supported copper catalyst or the supported copper/magnesium catalyst which is formed by supporting copper, or copper and magnesium, on a carrier composed of a magnesium-containing metal oxide. These catalysts may be used singly or in combination of any two or more thereof.

In addition, in the present invention, a catalyst containing a metal element belonging to Group VIII of the Periodic Table, calcium, barium, zinc, etc., may also be used as a co-catalyst. Among these co-catalysts, from the viewpoints of a high catalytic activity and a high selectivity of the catalyst, preferred are those catalysts composed of calcium, barium, zinc or palladium. These co-catalysts may be used singly or in combination of any two or more thereof. Also, these co-catalysts may be suitably incorporated into the catalyst containing copper and magnesium. Further, these co-catalysts may be used as a separate catalyst in the form of a mixture with the catalyst containing copper and magnesium.

The mass ratio of magnesium to copper (magnesium/copper) in the catalyst used in the present invention is from 0.01 to 20, preferably from 0.03 to 15, more preferably from 0.05 to 10, still more preferably from 0.05 to 5, further still more preferably from 0.05 to 1, and further still more preferably from 0.1 to 1.0 from the viewpoints of a high catalytic activity and a high selectivity of the catalyst. The mass ratio of the co-catalyst to copper (co-catalyst/copper) is preferably from 0.0005 to 0.5 and more preferably from 0.001 to 0.3 from the viewpoints of a high catalytic activity and a high selectivity of the catalyst. The content of copper in the catalyst is preferably from 5 to 70% by mass, more preferably 10 to 60% by mass and still more preferably from 15 to 55% by mass in terms of metallic copper from the viewpoint of a good catalytic activity.

The contents of the respective constitutional elements in the catalyst used in the present invention may be measured, for example, by the following procedure.

A sample weighed in an amount of 0.1 g is sampled in a special container for decomposition thereof. The sample is mixed with 2 mL of sulfuric acid and then heated. Further, appropriate amounts of hydrogen peroxide and nitric acid are added to the sample, and the resulting solution is heated again. These procedures are repeated until the solution becomes transparent. After cooling, the solution is transferred into a measuring flask, and pure water is added thereto to obtain 50 mL of a dilute solution. The thus obtained solution is subjected to ICP emission spectral analysis to measure the contents of the respective constitutional elements.

The method for producing the catalyst used in the present invention is not particularly limited, and may be appropriately selected from conventionally known methods such as, for example, an impregnation method, a precipitation method and an ion-exchange method depending upon kind of the carrier used.

The catalyst used in the present invention may be produced, for example, by the following method.

That is, an aqueous solution containing nitrates, sulfates, carbonates, chlorides, amine complexes, etc., of the respective metal elements is optionally mixed with a carrier. Then, an alkali aqueous solution containing a hydroxide, a carbonate or the like of sodium, potassium, etc., is dropped into the above solution or suspension to obtain a precipitate, and the thus obtained precipitate is subjected to solid-liquid separation by a suitable method such as filtration and centrifugal separation. Next, the obtained solid is washed with ion-exchanged water, dried and then calcined at a temperature of preferably from about 300 to about 1000° C. while flowing air therethrough and more preferably from 400 to 800° C. while flowing air therethrough, thereby producing the aimed catalyst in the form of a metal oxide.

The thus produced catalyst can exhibit a catalyst performance equal to or higher than that of the conventional copper/chromium catalysts. Therefore, by using such a catalyst, it is possible to reduce an amide compound under moderate conditions.

In the process for producing the tertiary amine according to the present invention, the amide compound represented by the above general formula (I) is reduced, preferably by hydrogenation reduction method, in the presence of the thus produced catalyst. The reduction reaction may be carried out in a hydrogen atmosphere under normal pressures or under a hydrogen-applied pressure, or in a flowing hydrogen under normal pressures or under applied pressure. The reaction may be conducted by either a continuous method or a batch method. In the batch method, the amount of the catalyst used is preferably from 0.01 to 20% by mass, more preferably from 0.05 to 20% by mass and still more preferably from 0.1 to 15% by mass on the basis of the raw amide compound from the viewpoints of a good reactivity, suppression of production of by-products and low production costs. The reaction temperature is preferably from 140 to 300° C. and more preferably from 160 to 270° C. from the viewpoints of enhancing the reactivity and suppressing production of by-products.

The reaction pressure in terms of a gauge pressure is usually from about normal pressures to about 25 MPaG, preferably from 0.1 to 5.0 MPaG, more preferably from 0.1 to 3.0 MPaG and still more preferably from 0.1 to 2.5 MPaG from the viewpoints of enhancing the reactivity and suppressing increase in burden of facilities. Further, from the viewpoints of enhancing the reactivity and suppressing production of by-products, the reaction is preferably carried out under a flowing hydrogen, and the amount of hydrogen flowing through the reaction system is preferably from 0.1 to 10.0 mol/h and more preferably from 0.1 to 5.0 mol/h per 1 mol of the raw amide.

The composition of the reaction product obtained in the hydrogen reduction reaction according to the present invention may be analyzed by gas chromatography.

Thus, when subjecting the amide compound represented by the general formula (I) to hydrogen reduction under moderate conditions, the tertiary amine represented by the general formula (II) which contains a less amount of by-products and has a high purity can be produced with a good productivity in an economically advantageous manner.

EXAMPLES

The present invention is described in more detail by referring to the following Examples, etc. However, it should be noted that the following Examples and Comparative Examples are only illustrative and not intended to limit the invention thereto.

Production Example 1

A separable flask was charged with 100 g of copper nitrate trihydrate and 69 g of magnesium nitrate hexahydrate. The contents of the flask were dissolved in 2 L of ion-exchanged water, and then heated to 50° C. while stirring. The flask was further charged with 33 g of synthesized zeolite ("ZEOLUM F-9" available from Tosoh Corporation), and the contents of the flask were heated to 90° C. Then, 724 g of a 10% sodium carbonate aqueous solution was dropped to the flask over 1 h, and the obtained reaction solution was aged for 1 h. The resulting suspended solution was cooled, and then subjected to filtration and washing with water, and further dried at 110° C. over a whole day and night. The resulting dried product was calcined at 600° C. for 1 h. As a result, it was confirmed that the mass ratio of magnesium to copper (magnesium/copper) in the obtained metal oxide was 0.25, and the content of copper in the catalyst was 34% by mass.

Production Example 2

A separable flask was charged with 33 g of magnesium oxide ("KYOWA-MAG 150" available from Kyowa Chemical Industry, Co., Ltd.). The contents of the flask were suspended in 1 L of ion-exchanged water, and then heated to 90° C. while stirring. Then, an aqueous solution prepared by dissolving 100 g of copper nitrate trihydrate in 500 mL of ion-exchanged water and 440 g of a 10% sodium carbonate aqueous solution were simultaneously dropped for 1 h into the resulting solution, and the obtained reaction solution was aged for 1 h. The resulting suspended solution was cooled, and then subjected to filtration and washing with water, and further dried at 110° C. over a whole day and night. The resulting dried product was calcined at 450° C. for 3 h. As a result, it was confirmed that the mass ratio of magnesium to copper (magnesium/copper) in the obtained metal oxide was 0.76, and the content of copper in the catalyst was 40% by mass.

Production Example 3

The same procedure as in Production Example 2 was repeated except for using, in addition to 100 g of copper nitrate trihydrate, 0.108 g of palladium chloride, and the calcination was conducted at 600° C. for 1 h. As a result, it was confirmed that the obtained product was a magnesia-supported copper/palladium catalyst in which the mass ratios of magnesium to copper (magnesium/copper) and palladium to copper (palladium/copper) were 0.76 and 0.0024, respectively, and the content of copper in the catalyst was 40% by mass.

Production Example 4

The same procedure as in Production Example 2 was repeated except for using, in addition to 100 g of copper nitrate trihydrate, 0.296 g of zinc nitrate hexahydrate, and the calcination was conducted at 600° C. for 1 h. As a result, it was confirmed that the obtained product was a magnesia-supported copper/zinc catalyst in which the mass ratios of magnesium to copper (magnesium/copper) and zinc to copper (zinc/copper) were 0.76 and 0.0025, respectively, and the content of copper in the catalyst was 40% by mass.

Production Example 5

The same procedure as in Production Example 2 was repeated except for using, in addition to 100 g of copper nitrate trihydrate, 0.388 g of calcium nitrate tetrahydrate, and the calcination was conducted at 600° C. for 1 h. As a result, it was confirmed that the obtained product was a magnesia-supported copper/calcium catalyst in which the mass ratios of magnesium to copper (magnesium/copper) and calcium to copper (calcium/copper) were 0.76 and 0.0025, respectively, and the content of copper in the catalyst was 40% by mass.

Production Example 6

The same procedure as in Production Example 5 was repeated except for using 12.4 g of barium nitrate in place of calcium nitrate tetrahydrate, and using 724 g of a 10% sodium carbonate aqueous solution as an alkali agent. As a result, it was confirmed that the obtained product was a magnesia-supported copper/barium catalyst in which the mass ratios of magnesium to copper (magnesium/copper) and barium to copper (barium/copper) were 0.76 and 0.25, respectively, and the content of copper in the catalyst was 36% by mass.

Production Example 7

The same procedure as in Production Example 1 was repeated except for using 100 g of copper nitrate trihydrate, 34.5 g of magnesium nitrate hexahydrate, and 33 g of synthesized hydrotalcite represented by the formula: $Mg_{4.5}Al_{12}(OH)_{13}CO_3 \cdot 3.5H_2O$ ("KYOWARD 1000" available from Kyowa Chemical Industry, Co., Ltd.) as a carrier. As a result, it was confirmed that the mass ratio of magnesium to copper (magnesium/copper) in the obtained metal oxide was 0.30, and the content of copper in the catalyst was 37% by mass.

Production Example 8

A separable flask was charged with 440 g of a 10% sodium carbonate aqueous solution and 33 g of magnesium oxide (commercial product available from Kishida Chemical Co., Ltd.). The contents of the flask were suspended in 1.5 L of ion-exchanged water, and then heated to 90° C. while stirring. Then, an aqueous solution prepared by dissolving 100 g of copper nitrate trihydrate in 500 mL of ion-exchanged water was dropped into the resulting solution over 1 h, and the obtained reaction solution was aged for 1 h. The resulting suspended solution was cooled, and then subjected to filtration and washing with water, and further dried at 110° C. over a whole day and night. The resulting dried product was calcined at 450° C. for 3 h. As a result, it was confirmed that the mass ratio of magnesium to copper (magnesium/copper) in the obtained metal oxide was 0.76, and the content of copper in the catalyst was 40% by mass.

Production Example 9

A separable flask was charged with 100 g of copper nitrate trihydrate and 15 g of magnesium nitrate hexahydrate. The contents of the flask were dissolved in 2 L of ion-exchanged water, and then heated to 50° C. while stirring. The flask was further charged with 33 g of synthesized zeolite ("ZEOLUM F-9" available from Tosoh Corporation), and the contents of the flask were heated to 90° C. Then, 724 g of a 10% sodium carbonate aqueous solution was dropped to the flask over 1 h, and the obtained reaction solution was aged for 1 h. The resulting suspended solution was cooled, and then subjected to filtration and washing with water, and further dried at 110° C. over a whole day and night. The resulting dried product was calcined at 600° C. for 1 h. As a result, it was confirmed that the mass ratio of magnesium to copper (magnesium/copper) in the obtained metal oxide was 0.05, and the content of copper in the catalyst was 38% by mass.

Production Example 10

The same procedure as in Production Example 1 was repeated except for using silica ("CARiACT Q-3" available from Fuji Silicia Chemical Co., Ltd.) in place of the synthesized zeolite. As a result, it was confirmed that the mass ratio of magnesium to copper (magnesium/copper) in the obtained metal oxide was 0.25, and the content of copper in the catalyst was 34% by mass.

Production Example 11

The same procedure as in Production Example 1 was repeated except for using alumina ("ALUMINA MGA" available from Mizusawa Industrial Chemicals Ltd.) in place of the synthesized zeolite. As a result, it was confirmed that the mass ratio of magnesium to copper (magnesium/copper) in the obtained metal oxide was 0.25, and the content of copper in the catalyst was 34% by mass.

Comparative Production Example 1

According to the procedure described in Production Example 2 of JP 2001-302596A, a comparative catalyst was produced and further calcined at 450° C. for 3 h. As a result, it was confirmed that the obtained product was a zeolite-supported copper/zinc catalyst in which the mass ratio of zinc to copper (zinc/copper) was 0.25, and the content of copper in the catalyst was 35% by mass.

More specifically, a separable flask was charged with 100 g of copper nitrate and 30 g of zinc nitrate. The contents of the flask were dissolved in 2 L of water, and then heated while stirring. The flask was further charged at 50° C. with 33 g of synthesized zeolite ("ZEOLUM F9" available from Tosoh Corporation), and then 546 g of a 10% $Na_2CO_3$ aqueous solution (content of $Na_2CO_3$: equimolar amount based on the metal salts) was dropped at 90° C. to the above obtained solution over 1 h. The resulting reaction solution was aged for 1 h. Thereafter, the obtained precipitate was subjected to filtration and washing with water, and further dried at 110° C. for 10 h. The obtained dried product was calcined at 600° C. for 1 h and then at 450° C. for 3 h, thereby obtaining a zeolite-supported copper/zinc catalyst.

Comparative Production Example 2

The same procedure as in Comparative Production Example 1 was repeated except for conducting the calcination at 600° C. for 1 h in place of the calcination at 450° C. for 3 h.

As a result, it was confirmed that the obtained product was a zeolite-supported copper/zinc catalyst in which the mass ratio of zinc to copper (zinc/copper) was 0.25, and the content of copper in the catalyst was 35% by mass.

Example 1

A rotary autoclave was charged with 300 g of N,N-dimethyl lauroyl amide and 5% by mass (on the basis of the raw amide compound) of the catalyst produced in Production Example 1. An inside of the autoclave was purged and replaced with nitrogen, and then hydrogen was introduced thereinto until an inside pressure of the autoclave reached 0.5 MPa. Thereafter, while maintaining the inside pressure of the autoclave at 0.5 MPa, hydrogen was introduced into the reaction system at a rate of 40 L/h (1.35 mol/h per 1 mol of the raw amide compound). Then, the reaction system was heated to 250° C. at which the hydrogen reduction reaction was conducted for 6 h. The obtained reaction product was subjected to filtration to remove the catalyst therefrom, and then the composition of the reaction product was analyzed by gas chromatography. The composition of the thus obtained reaction product is shown in Table 1.

Example 2 and Comparative Examples 1 and 2

The same procedure as in Example 1 was repeated except for using the catalyst produced in Production Example 2 or the catalyst produced in Comparative Production Example 1 or 2 in place of the catalyst produced in Production Example 1. The compositions of the respective reaction products are shown in Table 1.

TABLE 1

| | | | Composition of reaction product (mass %) | | | |
|---|---|---|---|---|---|---|
| | Kind of catalyst | Amide conversion rate (%) | Dimethyl lauryl amine | Dilauryl monomethyl amine | Lauryl alcohol | others |
| Example 1 | Production Example 1 | 70.3 | 56.8 | 6.4 | 3.3 | 3.8 |
| Example 2 | Production Example 2 | 79.2 | 66.0 | 5.8 | 3.1 | 4.3 |
| Comparative Example 1 | Comparative Production Example 1 | 51.3 | 41.3 | 3.3 | 4.2 | 2.5 |
| Comparative Example 2 | Comparative Production Example 2 | 68.8 | 55.5 | 4.7 | 3.3 | 5.3 |

Examples 3 to 11 and Comparative Examples 3 and 4

The same procedure as in Example 1 was repeated except that the respective catalysts produced in Production Examples 3 to 11 and Comparative Production Examples 1 and 2 were used in place of the catalyst produced in Production Example 1, and the hydrogen reduction reaction was conducted for the time period as shown in Table 2 while maintaining the reaction pressure at 1.5 MPaG. The respective obtained reaction products were subjected to filtration to remove the catalysts therefrom, and the compositions thereof were analyzed by gas chromatography. The compositions of the respective reaction products are shown in Table 2.

TABLE 2

| | | | | Composition of reaction product (mass %) | | | |
|---|---|---|---|---|---|---|---|
| | Kind of catalyst | Reaction time (h) | Amide conversion rate (%) | Dimethyl lauryl amine | Dilauryl monomethyl amine | Lauryl alcohol | others |
| Example 3 | Production Example 3 | 7.0 | 99.8 | 83.1 | 9.4 | 5.2 | 2.1 |
| Example 4 | Production Example 4 | 6.5 | 99.7 | 82.9 | 8.3 | 6.0 | 2.5 |
| Example 5 | Production Example 5 | 7.0 | 99.6 | 83.1 | 9.1 | 5.3 | 2.1 |

TABLE 2-continued

|  | Kind of catalyst | Reaction time (h) | Amide conversion rate (%) | Composition of reaction product (mass %) | | | |
|---|---|---|---|---|---|---|---|
|  |  |  |  | Dimethyl lauryl amine | Dilauryl monomethyl amine | Lauryl alcohol | others |
| Example 6 | Production Example 6 | 9.0 | 98.2 | 82.7 | 4.3 | 8.1 | 3.1 |
| Example 7 | Production Example 7 | 6.5 | 98.5 | 81.9 | 5.2 | 8.7 | 2.7 |
| Example 8 | Production Example 8 | 7.5 | 99.8 | 83.8 | 7.9 | 6.5 | 1.6 |
| Example 9 | Production Example 9 | 9.0 | 95.1 | 78.2 | 10.3 | 4.6 | 2.0 |
| Example 10 | Production Example 10 | 9.0 | 96.7 | 77.2 | 5.4 | 10.1 | 4.0 |
| Example 11 | Production Example 11 | 9.0 | 97.8 | 81.6 | 8.2 | 5.4 | 2.6 |
| Comparative Example 3 | Comp. Production Example 1 | 9.0 | 75.1 | 57.6 | 7.5 | 5.6 | 4.4 |
| Comparative Example 4 | Comp. Production Example 2 | 9.0 | 89.1 | 73.4 | 4.9 | 7.4 | 3.4 |

Example 12

The same procedure as in Example 1 was repeated except that the catalyst produced in Production Example 7 was used in place of the catalyst produced in Production Example 1, and hydrogen was introduced into the reaction system at a rate of 20 L/h (0.68 mol/h per 1 mol of the raw amide) while maintaining the reaction pressure at 1.5 MPaG. The obtained reaction product was subjected to filtration to remove the catalyst therefrom, and the composition thereof was analyzed by gas chromatography. As a result, it was confirmed that the amide conversion rate was 90.1%, and the reaction product contained 79.5% of dimethyl lauryl amine, 4.6% of dilauryl monomethyl amine and 4.6% of lauryl alcohol.

Example 13

In the procedure of Example 12, when the reaction was continued for 9 h, the conversion rate of the raw amide reached its detection limit or lower as measured by gas chromatography. As a result, it was confirmed that the resulting reaction product contained 86.5% of dimethyl lauryl amine, 6.6% of dilauryl monomethyl amine and 5.4% of lauryl alcohol.

Example 14

The same procedure as in Example 12 was repeated except that the catalyst produced in Production Example 7 was charged in an amount of 3% by mass (on the basis of the raw amide compound), and hydrogen was introduced into the reaction system at a rate of 40 L/h (1.35 mol/h per 1 mol of the raw amide) to conduct the hydrogen reduction reaction for 9 h. The obtained reaction product was subjected to filtration to remove the catalyst therefrom, and the composition thereof was analyzed by gas chromatography. As a result, it was confirmed that the amide conversion rate was 93.0%, and the reaction product contained 79.9% of dimethyl lauryl amine, 3.2% of dilauryl monomethyl amine and 8.1% of lauryl alcohol.

Example 15

The same procedure as in Example 1 was repeated except for using 300 g of N,N-dimethyl stearoyl amide in place of N,N-dimethyl lauroyl amide, and using the catalyst produced in Production Example 2 in place of the catalyst produced in Production Example 1. The obtained reaction product was subjected to filtration to remove the catalyst therefrom, and the composition thereof was analyzed by gas chromatography. As a result, it was confirmed that the amide conversion rate was 74.3%, and the reaction product contained 60.2% of dimethyl stearyl amine, 4.1% of distearyl monomethyl amine and 7.7% of stearyl alcohol.

Meanwhile, the contents of the respective metal atoms in the above Examples, etc., were measured by the above ICP emission spectral analysis using "JY238" available from Jobin Ybon Inc.

Also, the gas chromatographic analysis of the respective compositions was carried out using the following apparatuses.

Gas Chromatograph: HEWLETT PACKARD Series 6890
Column: "DB-17" available from J & W Inc. (inner diameter: 0.25 mm× length: 15 m× film thickness: 0.5 μm)

INDUSTRIAL APPLICABILITY

According to the production process of the present invention, the high-purity aliphatic tertiary amine containing a less amount of by-products can be produced with a good productivity in an economically advantageous manner. The aliphatic tertiary amine produced according to the process of the present invention can be suitably used as an intermediate product for fabric softeners, antistatic agents, additives for gasoline, shampoos, rinses, bactericides, detergents, etc., in extensive domestic and industrial application fields.

The invention claimed is:

1. A process for producing a tertiary amine represented by formula (II):

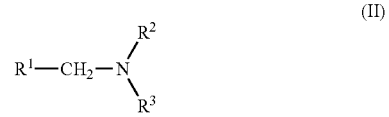
(II)

wherein $R^1$ is a linear or branched aliphatic hydrocarbon group having 5 to 23 carbon atoms; and $R^2$ and $R^3$ are each independently a linear or branched alkyl group having 1 to 6 carbon atoms and may be the same or different, said process comprising reducing an amide compound represented by formula (I):

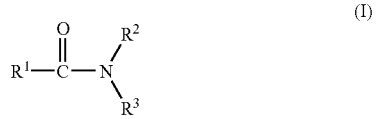

wherein $R^1$, $R^2$ and $R^3$ are the same as defined above,
in the presence of a catalyst comprising copper and magnesium at a mass ratio of magnesium to copper (magnesium/copper) of from 0.01 to 20.

2. The process according to claim 1, wherein a content of the copper in the catalyst is from 5 to 70% by mass in terms of metallic copper.

3. The process according to claim 1, wherein the catalyst further comprises at least one element selected from the group consisting of a metal element belonging to Groups VIII of the Periodic Table, calcium, barium and zinc.

4. The process according to claim 3, wherein a mass ratio of the at least one element selected from the group consisting of a metal element belonging to Groups VIII of the Periodic Table, calcium, barium and zinc, to the copper (at least one element selected from the group consisting of a metal element belonging to Groups VIII of the Periodic Table, calcium, barium and zinc/copper) in the catalyst is from 0.0005 to 0.5.

5. The process according to claim 1, wherein the catalyst is a supported copper/magnesium catalyst which is formed by supporting copper and magnesium on a carrier comprising at least one material selected from the group consisting of silica, alumina, zeolite and diatomaceous earth, or the catalyst is a supported copper catalyst or a supported copper/magnesium catalyst which is formed by supporting copper, or copper and magnesium, on a carrier comprising a magnesium-containing metal oxide.

6. The process according to claim 1, wherein the amide compound represented by formula (I) is reduced by flowing hydrogen in an amount of from 0.1 to 10 mol/h per 1 mol of the amide compound.

7. The process according to claim 1, wherein the catalyst is used in an amount of from 0.01 to 20% by mass on the basis of the amide compound represented by formula (I).

8. The process according to claim 1, wherein a mass ratio of magnesium to copper (magnesium/copper) of from 0.05 to 5.

9. The process according to claim 1, wherein a mass ratio of magnesium to copper (magnesium/copper) of from 0.05 to 1.

10. The process according to claim 1, wherein a mass ratio of magnesium to copper (magnesium/copper) of from 0.1 to 1.0.

11. The process according to claim 1, wherein a content of the copper in the catalyst is from 10 to 60% by mass in terms of metallic copper.

12. The process according to claim 1, wherein a content of the copper in the catalyst is from 15 to 55% by mass in terms of metallic copper.

13. The process according to claim 4, wherein said mass ratio is from 0.001 to 0.3.

14. The process according to claim 6, wherein hydrogen is in an amount of from 0.1 to 5.0 mol/h per 1 mol of the amide compound.

15. The process according to claim 1, wherein a reaction temperature is from 140 to 300° C.

16. The process according to claim 1, wherein a reaction temperature is from 160 to 270° C.

17. The process according to claim 1, wherein said a reaction pressure in terms of gauge pressure is from about normal pressures to about 25 MPaG.

18. The process according to claim 1, wherein said a reaction pressure in terms of gauge pressure is from 0.1 to 5.0 MPaG.

19. The process according to claim 1, wherein said a reaction pressure in terms of gauge pressure is from 0.1 to 3.0 MPaG.

20. The process according to claim 1, wherein said a reaction pressure in terms of gauge pressure is from 0.1 to 2.5 MPaG.

* * * * *